United States Patent [19]
Errico et al.

[11] Patent Number: 5,709,684
[45] Date of Patent: *Jan. 20, 1998

[54] ADVANCED COMPRESSION LOCKING VARIABLE LENGTH CROSS-LINK DEVICE

[75] Inventors: Joseph P. Errico, Far Hills; Thomas J. Errico, Summit,; James D. Ralph, Oakland, all of N.J.

[73] Assignee: Fastenetix, LLC, Summit, N.J.

[*] Notice: The term of this patent shall not extend beyond the expiration date of Pat. No. 5,667,507.

[21] Appl. No.: 632,561

[22] Filed: Apr. 15, 1996

Related U.S. Application Data

[63] Continuation-in-part of Ser. No. 567,144, Dec. 4, 1995.
[51] Int. Cl.$^6$ ............................................. A61B 17/70
[52] U.S. Cl. .................................... 606/61; 606/72
[58] Field of Search ........................... 606/60, 61, 63, 606/64, 72, 73

[56] References Cited

U.S. PATENT DOCUMENTS

| | | | |
|---|---|---|---|
| 4,611,582 | 9/1986 | Duff | 128/69 |
| 5,005,562 | 4/1991 | Contrel . | |
| 5,108,395 | 4/1992 | Laurain | 606/73 |
| 5,147,360 | 9/1992 | Dubousset | 606/61 |
| 5,154,718 | 10/1992 | Cozad et al. | 606/61 |
| 5,439,463 | 8/1995 | Lin | 606/61 |
| 5,549,607 | 8/1996 | Olson et al. | 606/61 |

Primary Examiner—Michael Buiz
Assistant Examiner—Daphna Shai
Attorney, Agent, or Firm—Joseph P. Errico, Esq.

[57] ABSTRACT

A variable length cross-link device for use with orthopaedic dual rod apparatuses includes a pair of elongate elements, each having a first end which mates with a rod or pedicle screw. The first element has a second end which is narrow and extending. The second element has a second end which is wide and extending, and includes a through hole. The invention further includes a post having an upper threaded portion mounted through the hole in the second element, and a passageway in the lower portion for receiving the second end of the first element. A nut is provided onto the post. Prior to tightening of the nut, the first element is slidable relative to the post and the second element, and the post element has rotational freedom within the through hole such that the first and second elements may be angulated relative to one another. Once the nut is tightened, the first and second elements are compressibly engaged, thereby crush locking the elements together. In a first embodiment, the first ends of the elongate elements are curvate and have set screw hole to hook and lock onto the rods. In a second embodiment the first ends have eyeloops for coupling to the heads of pedicle screws. In a third embodiment, which is compatible with either of the first end configurations, the narrow and extending end of the first element is cylindrical so that the first and second ends may axially rotate relative to one another.

16 Claims, 13 Drawing Sheets

ADVANCED COMPRESSION LOCKING VARIABLE LENGTH CROSS-LINK DEVICE

CROSS-REFERENCE TO RELATED APPLICATION

This application is a continuation-in-part of U.S. patent application Ser. No. 08/567,144, Dec. 4, 1995 entitled "A Compression Locking Variable Length Cross-Link Device For Use With Dual Rod Apparatus".

BACKGROUND OF THE INVENTION

1. Field of the Invention

This invention relates generally to a mechanical cross-link device for use with dual rod orthopaedic implant apparatus. More particularly, this invention relates to a novel device which may be fixed to each rod of a dual rod implant apparatus, or to the pedicle screws thereof, for maintaining and enhancing the rigidity of the apparatus.

2. Discussion of the Prior Art

The bones and connective tissue of an adult human spinal column consist of an upper portion (the cervical, thoracic, and lumbar regions) having more than 20 discrete bones, and a lower portion which consists of the sacral bone and the coccygeal bodies. The bones of the upper portion are generally similar in shape, as will be more fully described hereinbelow with respect to FIGS. 1, 2 and 3. For the purpose of describing this invention, the sacral bone shall be distinguished from the spinal column; the spinal column, therefore, comprising for the purposes of this description, only the cervical, thoracic, and lumbar vertebrae.

Figure 1:
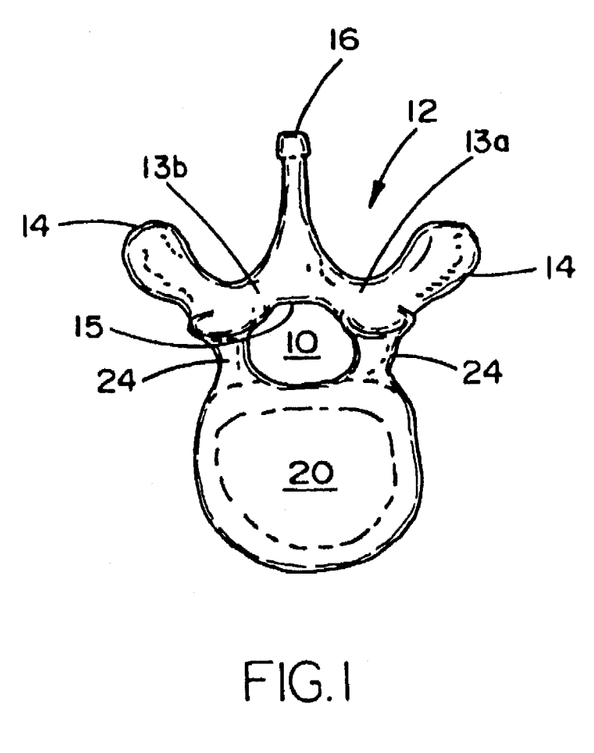
FIG. 1 is a top view of a vertebra of the human spine.
Figure 2:
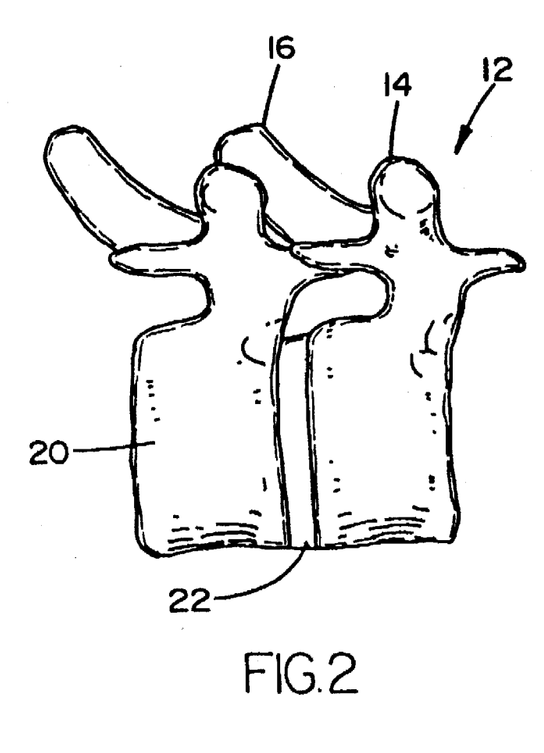
FIG. 2 is a side view of a sequence of vertebrae of the human spine.
Figure 3:
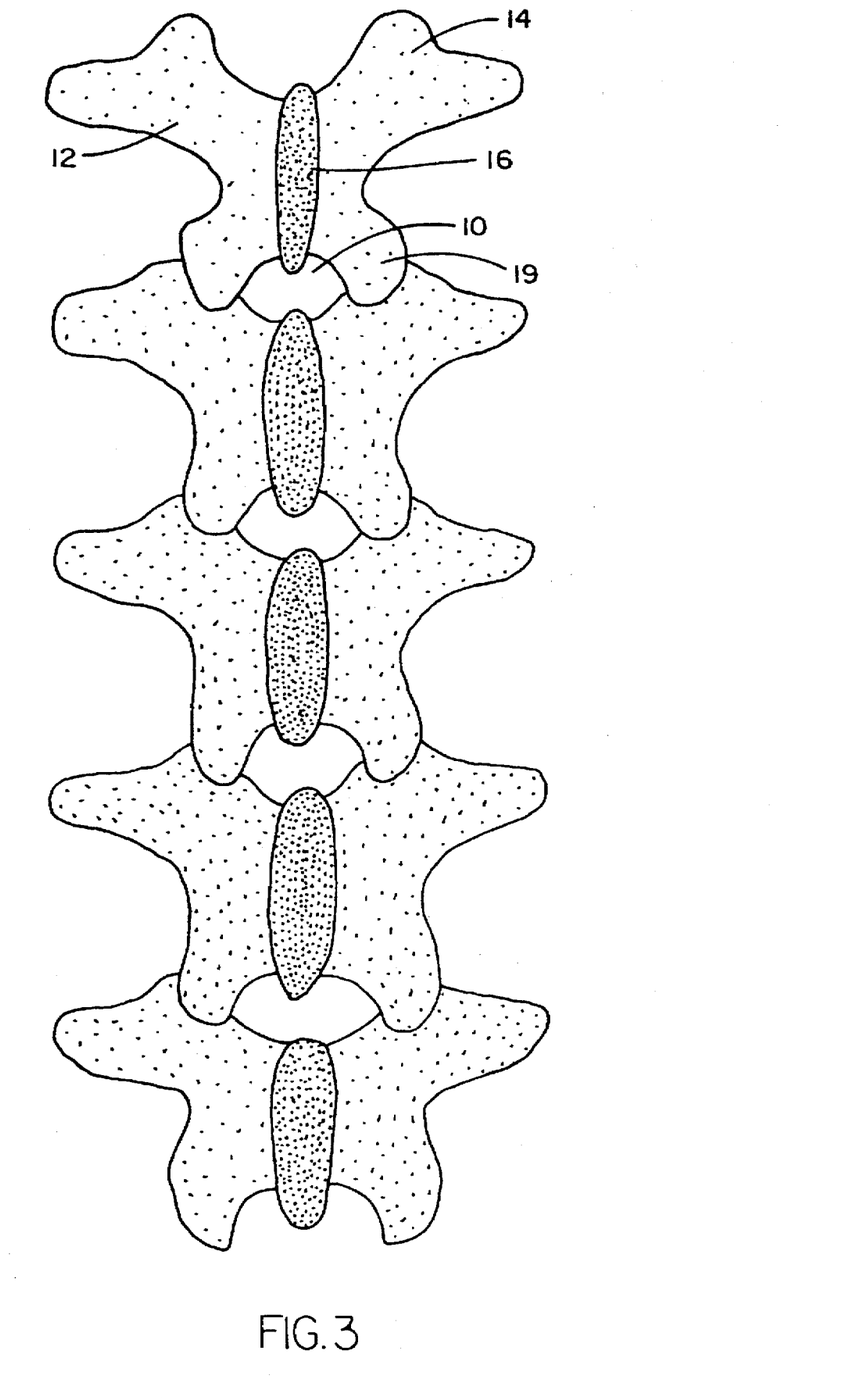
FIG. 3 is a posterior view of a sequence of vertebrae of the human spine.

The vertebrae vary in size, but are each similarly coupled to adjacent bones by a tri-joint complex. The tri-joint complex consists of an anterior disc and the two posterior facet joints, the anterior discs of adjacent bones being cushioned by cartilage spacers referred to as intervertebral discs. Referring now to FIGS. 1, 2 and 3, top, lateral, and posterior views of a typical vertebral bones of the spinal column are shown. The spinal cord is housed in the central canal 10, protected from the posterior side by a shell of bone called the lamina 12. The lamina 12 has three large protrusions, two of these extend laterally from the side ends thereof and are referred to as the transverse processes 14. The third extends back and down from the center of the lamina and is called the spinous process 16. The lamina 12 defines an arched shape about the posterior of the spinal cord, the arched shape having lateral portions 13a,13b which are generally straight, and which meet beneath the spinous process at a curved surface 15.

The anterior portion of the spine comprises a set of generally cylindrically shaped bones which are stacked one on top of the other. These portions of the vertebrae are referred to as the vertebral bodies 20, and are each separated from the other by the intervertebral discs 22. Pedicles 24 are bone bridges which couple the anterior vertebral body 20 to the corresponding lamina 12 and posterior elements 14,16.

Referring specifically to FIG. 3, the stacking of vertebrae is shown from the posterior. From the posterior, each vertebra is coupled to the one above and below via facet joints 19 on either side of an opening into the spinal canal 10.

In its entirety, the spinal column is highly complex in that it houses and protects critical elements of the nervous system which have innumerable peripheral nerves and arterial and venous bodies in close proximity. In spite of these complexities, the spine is a highly flexible structure, capable of a high degree of curvature and twist through a wide range of motion. Genetic or developmental irregularities, trauma, chronic stress, tumors, and disease, however, can result in spinal pathologies which either limit this range of motion, or which threaten the critical elements of the nervous system housed within the spinal column. A variety of systems have been disclosed in the art which achieve this immobilization by implanting artificial assemblies in or on the spinal column.

A variety of systems have been disclosed in the art which achieve this immobilization by implanting artificial assemblies in, or on, the spinal column. These assemblies may be classified by their position relative to the spine, as anterior, posterior, or lateral implants. Anterior and lateral assemblies generally comprise short structures which support only a few adjacent vertebral bodies. Conversely, posterior implants often comprise pairs of elongate vertically aligned rods for stabilizing both short and long segments of the spine. Such posterior rods are coupled to the back of the spinal column via hooks which slip under the lamina, means for attaching to the transverse process, and/or by screws which are inserted through the pedicle bone. In order to provide enhanced torsional rigidity, these apparatuses generally include cross-linking devices which couple the rods together transverse to the axis (vertical axis) of the apparatuses. These cross-linking devices may couple directly to the rods themselves, or may be attached to the pedicle screws.

Figure 4:
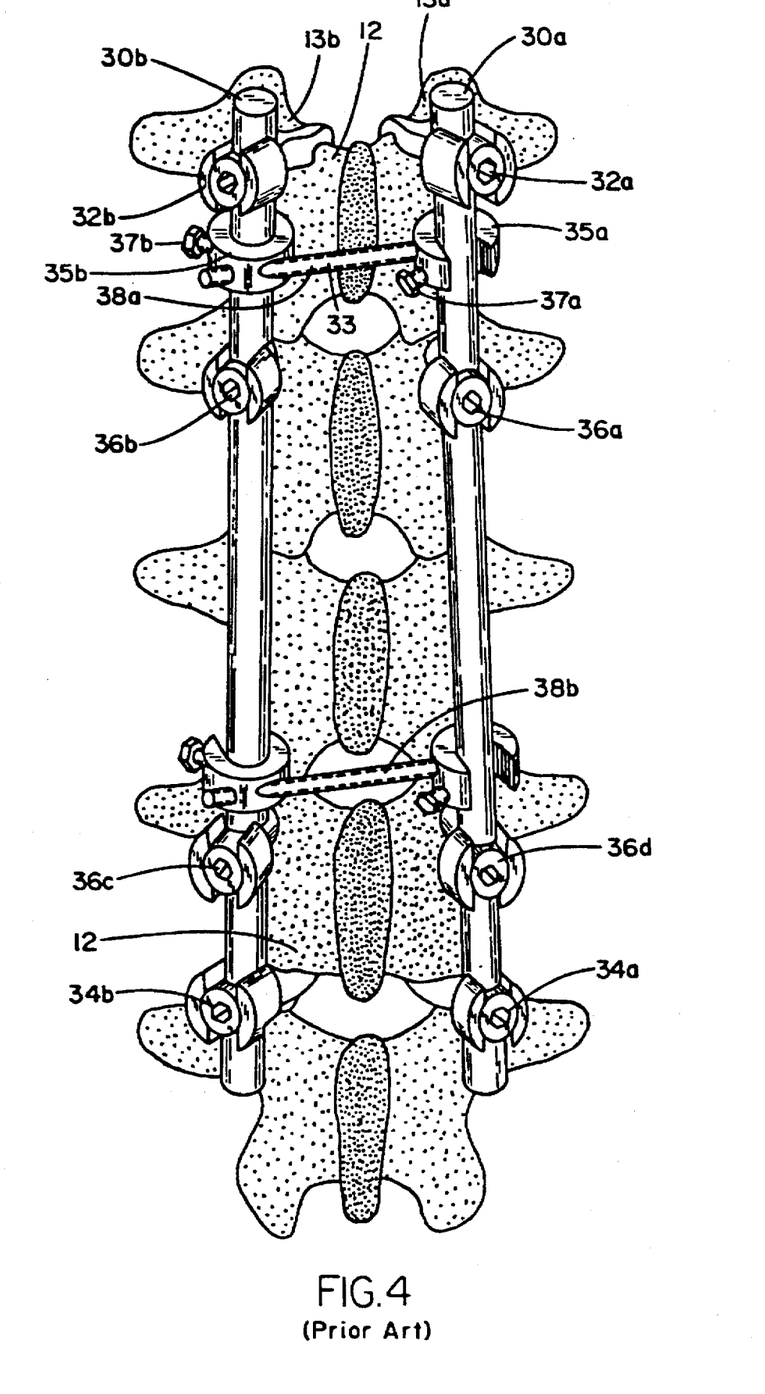
FIG. 4 is a posterior view of a dual rod apparatus of a prior art instrumentation as set forth in U.S. Pat. No. 5,005,562 to Cotrel, including cross-link devices.

Referring now to FIG. 4, U.S. Pat. No. 5,005,562 to Cotrel teaches such a dual rod apparatus which includes a pair of rods 30a,30b, which are each coupled to the spine via hooks 32a,34a and 32b,34b, respectively, as well as pedicle screws 36a,36d and 36b,36c, respectively. The rods 30a,30b are further stabilized by cross-link devices 38a,38b. These cross-link devices 38a,38b each include a pair of U-shaped gripping element 35a,35b which may receive the rod 30a, 30b respectively. Each of the gripping elements includes a first threaded hole which extends from the outer lateral surface into the inner surface of the U-shaped rod receiving region. The gripping elements 35a,35b are fixed to the rods 30a,30b by set screws 37a,37b which are positioned in the first holes such that tightening of the set screws locks the rod 30a,30b in the gripping element. The gripping elements 35a,35b are coupled together by a threaded rod 33 which permits the gripping elements to be selectively spread or brought closer together, in accordance with the relative position of the rods 30a,30b. The threaded rod 33 extends through a second set of threaded holes in the gripping elements 35a,35b.

The bulkiness of each of the gripping elements 35a,35b, required so that it may receive the threaded rod 33, is difficult for the surgeon to use easily under operative conditions. The size of the gripping elements, and the relative position of the set screws often cause substantial difficulty with respect to the tightening of same because of their positions relative to the operative access. This bulkiness also reduces available bone graft surface area, which is critical for a successful fusion and long term immobilization. In addition, in order for a surgeon to selectively vary the spread of the gripping elements 35a,35b, one of the gripping elements must be rotated relative to the other, thus requiring the cross-link to be removed (loosening the set screws and withdrawing the device entirely from the operative site). This is particularly burdensome with respect to providing the surgeon with the ability to apply an inward force to the rods 30a,30b as the spread may not be varied in situ.

It is therefore, a principal object of the present invention to provide a new and novel cross-link device which provides a less bulky profile, therein providing increased area for bone grafting.

It is also an object of the present invention to provide a cross-link device which provides the surgeon with the ability to lock the device to the rods or to the pedicle screws more easily than prior cross-link devices.

It is also, therefore, an object of the present invention to provide a cross-link device which provides the surgeon with the ability to vary the spread of the rod or pedicle gripping portions easily.

Other objects of the present invention not explicitly stated will be set forth, and will be more clearly understood, in conjunction with the descriptions of the preferred embodiments disclosed hereafter.

SUMMARY OF THE INVENTION

In its various embodiments, the preceding objects of the invention are achieved by the present invention which is a compression locking variable length cross-link device which may be affixed to the rods, or pedicle screws, of a dual rod implant apparatus. The present invention may be practiced in a variety of different embodiments; the several enclosed herein being representative of preferred ones of the invention.

The invention includes a pair of elements formed of a substantially rigid material, for example medical grade steel or titanium. In a first category of this invention, the elements each have first ends which are curvate so as to securely seat against and hook to the lateral outside surface of a rod of a dual rod apparatus. These curvate ends further include a through hole for receiving a set screw. The set screw positioned therein is designed to be threadably tightened downward onto the rod against which the first end is seated, therein locking the rod and element together.

In a second category of embodiments, the first ends have eyeloops enabling them to be mounted about respective pedicle screws, and secured in place by the downward pressure supplied by top locking nuts mounted thereon.

With respect to both of these categories, however, the second ends of the two elements are designed to be coupled together by a threaded post, which shall be described more fully hereinafter. One of the elements of the pair, referred to hereinafter as the first element comprises a flat second end which is narrowed to a width which is substantially less than the width of the flat material of which the rod securing end is formed (the thickness and corresponding structural strength of the flat end is desirably the same as that of the rod securing end). In addition, it is desirable for the top surface of this flat second end to have a grooved or roughened conformation, for example a diamond knurling.

With respect to the other of the elements (hereinafter referred to as the second element), the second end is also flat, but is wider. This widened portion includes a through hole having a diameter sufficient to receive the above-introduced threaded post. In addition, the undersurface of the flat second end of the second rod securing element is correspondingly roughened, for example, with a diamond knurl.

The coupling of these two elements is achieved by the incorporation of a threaded post. This threaded post is generally cylindrical and comprises a widened base, an intermediate portion having a passageway defined therethrough which is transverse to the axis of the post, and a threaded upper portion. The flat second end of the first element is inserted through the passageway, such that the knurled upper surface of the flat end is oriented upward. The threaded upper portion of the post is positioned through the hole in the flat portion of the second element such that the knurled lower and upper surfaces of the flat ends of the first and second elements contact on another. A top locking nut is then threaded onto the upper portion of the post.

Prior to the tightening of the nut, the flat end of the first element may slide relative to the flat portion of the second, so that the rod securing portions may be spread or drawn together in accordance with the positioning of the rods. Tightening of the nut down onto the top surface of the second flat portion causes the post to be drawn upwards until the roughened surfaces of the first and second flat portions seat and lock to one another under the compressive force.

It shall be understood, from the nature of the coupling of the two elements via the post member, that the two elements need not be co-linear to be secured. Rather, it is a feature of this invention, in the variations of the first and second category, for the element to be selectably variable in coupling angle in a given plane such that the device may form a non-linear cross-linking structure between two rods.

In a third category of embodiments of the present invention, the capacity to selectively vary the coupling angle is enhanced inasmuch as one of the pair of elements (the first) may be rotated about its elongate axis so that it may accomodate rods which are not co-planar. This variability is achieved by having the second end of the first element be cylindrical, and for the passageway formed in the post, in which the second end is to be inserted, to be correspondingly round so that the cylindrical end may rotate therein. The cylindrical end and the interior of the passageway may each include a diamond knurling so that they may mutually lock under the compressive forces applied by the second element via the upward drawing of the post element.

It shall be understood that this third category of devices may be affixed to the rods as are the embodiments of the first category, or may be coupled via the pedicle screws as are the embodiments of the second category.

BRIEF DESCRIPTION OF THE DRAWINGS

FIG. 10a is a side perspective view of a fully assembled embodiment of the present invention comprising all of the elements illustrated in FIGS. 5a, 6–8, and 9a;

DETAILED DESCRIPTION OF THE PREFERRED EMBODIMENT

While the present invention will be described more fully hereinafter with reference to the accompanying drawings, in which particular embodiments and methods of implantation are shown, it is to be understood at the outset that persons skilled in the art may modify the invention herein described while achieving the functions and results of this invention. Accordingly, the descriptions which follow are to be understood as illustrative and exemplary of specific structures, aspects and features within the broad scope of the present invention and not as limiting of such broad scope.

Figure 5A:
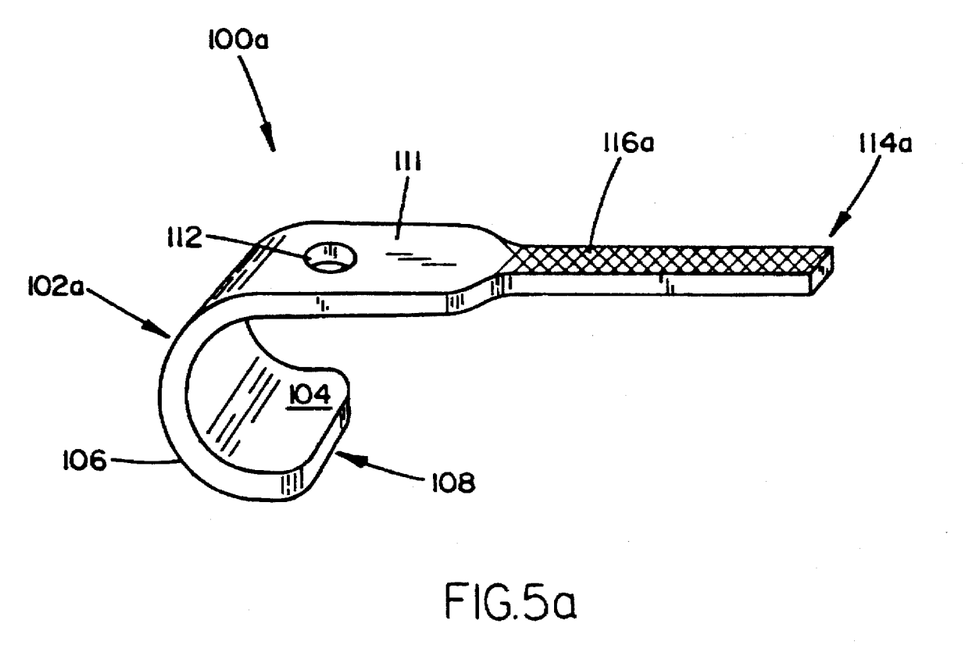
FIGS. 5a and 5b are side perspective views of first elements which are, respectively, aspects of embodiments of the first and second categories of the present invention.

Referring now to FIG. 5a, a first rod coupling element 100a of the first embodiment of the present invention is provided in a side perspective view. As with all elements of this invention, the material of which this rod hooking element may comprise a high strength material, for example medical grade steel or titanium compounds, which has been found ideally suited for implantation into the human body. The rod coupling element 100a shown in FIG. 5a is specifically formed of a thin and flat sheet of metal, the first end 102a of which has been curved to the shape of a hook. The hook has a semi-circular curvature defined by an inner surface 104 and an outer surface 106. The lower portion 108 of the semi-circular hook extends tangentially for a small distance, parallel to the remainder of the element. The curve is semi-circular so that it can cup and hook to the lateral outside surface of a first rod of a dual rod apparatus.

The top portion 111 of the first end 102a comprises a through hole 112 which is threaded and extends from a point on the top surface of the first end 102a which is to adjacent to the initial curvature of the hook to the underside of the same. Inasmuch as a set screw (set forth with respect to FIG. 6) is to be directed therethrough to lock the element 100a, and more specifically the first end 102a thereof, to a rod of the implant assembly, the through hole 112 may be angled such that the insertion and subsequent tightening of the set screw drives same toward the inner surface 104 of the hook. Such a preset angle of the through hole orientation enhances the locking strength of the set screw by increasing the cupping surface against which the rod is crushed.

The other end 114a of the rod coupling element comprises a narrowed and flat portion which has a width which is substantially reduced as compared with that of the first rod securing end 102a. The thickness and corresponding structural strength of this second end 114a is, however, desirably the same as that of the rod securing end. The top surface 116a of this second narrowed end 114a includes a roughening, for example a diamond knurling, which provides a greater coefficient of static friction to it; this enhanced friction coefficient being desirable for the purposes of compression locking this top surface against another surface.

Figure 6:
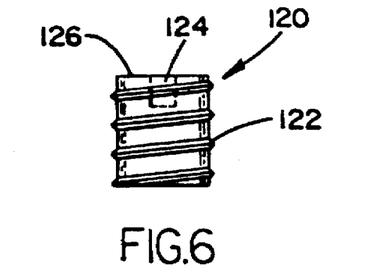
FIG. 6 is a side view of a set screw which is another aspect of the present invention.

Referring now to FIG. 6, a side view of the set screw 120 which is used to lock the rod to the first end 102a of the rod coupling element 100a (and for applying a compression pressure as described in regards to the second embodiment set forth herein) is provided. The set screw 120 comprises a surface threading 122 which is ideally suited to the threading of the through hole 112. The screw 120 further includes a recess 124 in the top 126 thereof, the recess having an internal conformation which may be engaged by a suitable tool for applying a torsional force thereto, for example a slot for a screwdriver or a hexagonally angled interior wall for an allen wrench.

Figure 7:
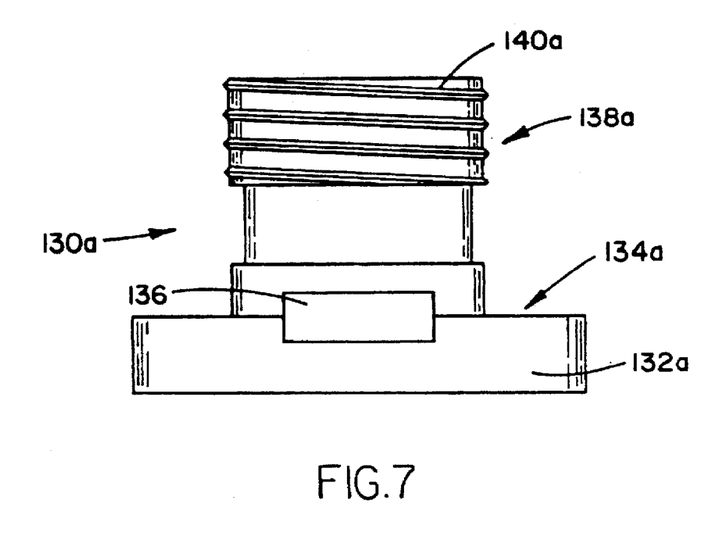
FIG. 7 is a side view of a post which is also used in conjunction with embodiments of the first and second categroies of the present invention.
Figure 8:
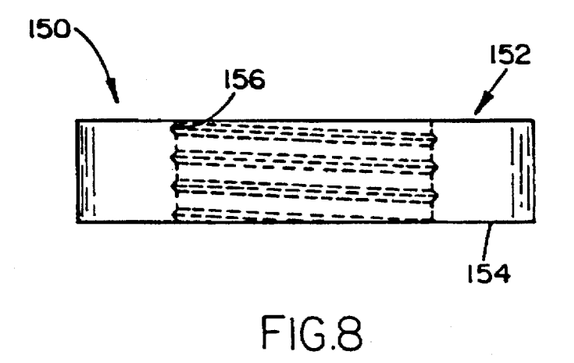
FIG. 8 is a side view of a top locking nut which threadably mates to an upper portion of the post of FIG. 7.

Referring now to FIGS. 7 and 8, side view of the post 130a and the top locking nut 150, which together provides the compression coupling of the elements of this embodiment is provided. Specifically referring to FIG. 7, the post 130a has a generally cylindrical shape. The base 132a of the post is wider than the upper portions, forming an annular flange 134a. This annular flange 134a may include a surface roughening so that it may have an enhanced gripping strength against any surface against which it might be compressed.

The upper portion of the base 132a, and the lower portion of the intermediate section of the post 130a includes a passageway 136 which extends transverse to the axis of the post, and which has a substantially rectangular cross-section. This passageway 136 is ideally suited for slidably receiving therethrough the flat extending end 114a of the first rod coupling element 100a (see FIG. 5a). The height of the passageway 136 is desirably slightly larger than the thickness of the flat extending end 114a, but the width of the passageway 136 is desirably the same. These dimensions eliminate any rotation or angulation of the first rod hooking element 100a relative to the post 130a.

The upper portion 138a of the post 130a extends upward from the passageway 136 and the intermediate portion, and comprise a threading 140a which is ideally suited for receiving thereon a top locking nut. With reference to FIG. 8, the top locking nut 150 comprises a top surface 152 and a bottom surface 154, and an interior threading 156.

Figure 9A:
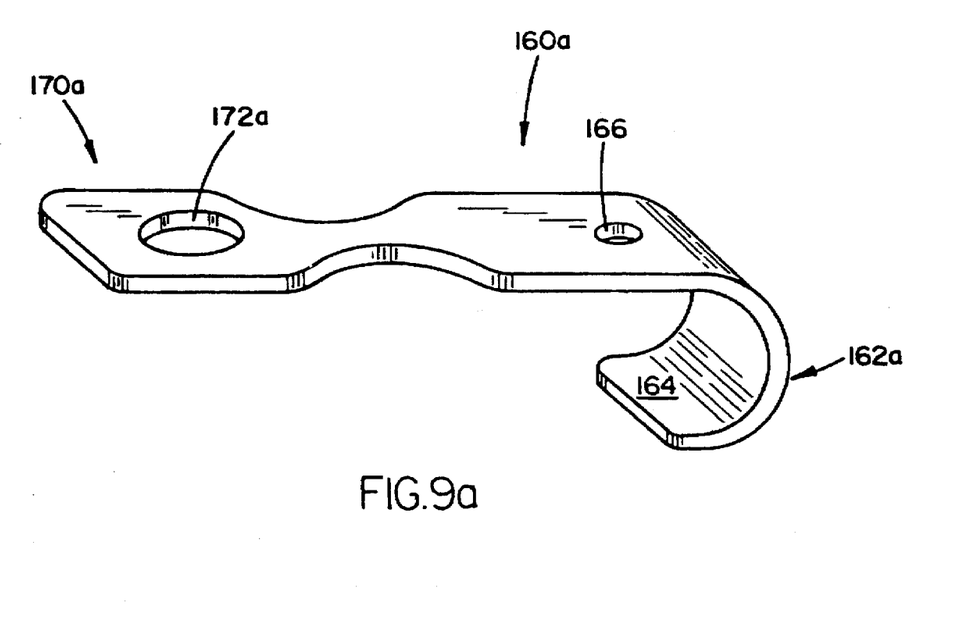
FIGS. 9a and 9b are side perspective views of two embodiments of second rod coupling element, each of which is an aspect of the present invention.

Referring now to FIG. 9a, a first embodiment of the second rod coupling element 160a is provided in a side perspective view. The second element 160a includes a rod securing end 162a which is substantially similar to the equivalent feature 102a of the first element 100a. More specifically, the rod securing end 162a thereof has a curvate shape and an interior surface 164 for seating against lateral outside surface the second rod of the dual rod apparatus. This curvate end 162a includes a through hole 166 for receiving a set screw 120 for locking the rod to the curvate shaped end.

The other end 170a of this second rod hooking element 160a is substantially wider than the flat end 114a of the first element 100a. The undersurface of this end 170a (not shown) may comprise a surface roughening similar to, or at least ideally suited for engaging, the roughened top surface 116a of the first element. This end 170a comprises a through hole 172a which has a width equal to or greater than the width of the upper threaded portion 1389, and the intermediate portions of the post 1309.

Figure 10A:
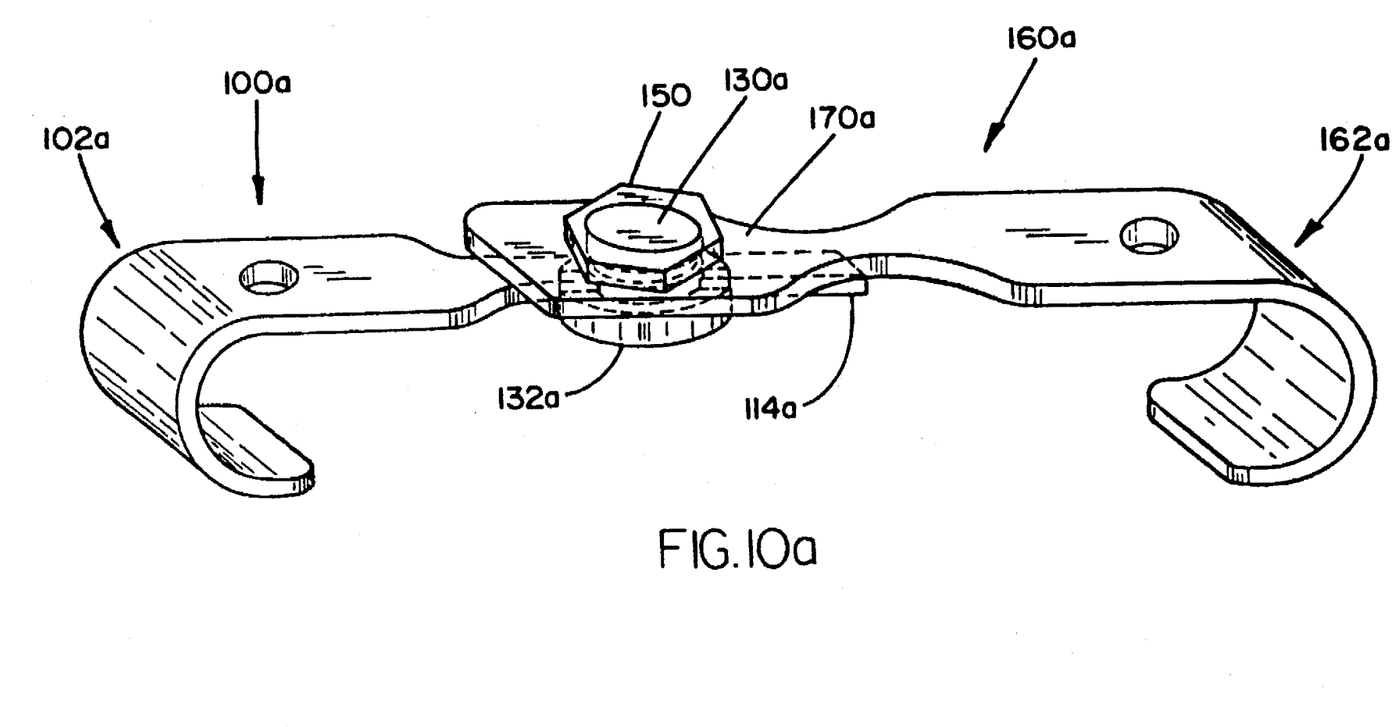

With additional reference now to FIG. 10a, in which a fully assembled first embodiment of the present invention is provided in a side perspective view, the method of assembly and the locking of the elements is described. First the proper site on the rods for the fixation of the cross-link device is identified by the surgeon. The site should provide enough space along the rods for engagement of rod securing ends 102a and 162a. Once this site is found, and the space separating the rods is cleared of all obstacles (for example, the spinous process) the narrow and flat extending portion 114a of the first element 100a is inserted into the passageway 136 of the post 130a, such that the roughened top surface 116a of the extending portion 114a is oriented in the direction of the upper section 138a of the post 130a.

Once the flat extending portion 114a has been inserted, the upper section 138a of the post 130a is inserted through the hole 172a in the rod coupling flat extending portion 170a of the second element 160a. The post 130a is inserted upwardly so that the top locking nut 150, and more specifically the threads 156 thereof, may engage the threads 140a of the upper portion 138a. Initial tightening of the nut 150 downward on the post 130a causes the bottom surface 154 of the nut to seat against the top surface of the flat extending portion 170a. At this point the flat extending portion 114a of the first element 100a remains slidable relative to both the post 130a and the second element 160a. The rod securing portions 102a and 162a may be selectively spread or drawn together by an amount determined solely by the length of the flat extending portion 114a of the first element 100a.

In addition, it may be understood that inasmuch as the post 130a is not secured to the through hole 172a, the post may be rotated, thus angulating the first and second elements 100a and 160a relative to one another from their co-linear orientation, within a plane defined thereby. While minimal rotation is desired, so as to maximize the contact surfaces of the extending portions 114a and 170a, slight angulations may be useful in cases wherein the rods are not locally parallel, but comprise a small convergence or divergence.

Continued tightening of the nut 150, however, causes the post 130a to be drawn upwards through the hole 172a, thereby causing the intermediate section, and the passageway 136 thereof to be similarly drawn upwards. In doing so, the roughened top surface 116a of the narrowed flat extending portion 114a is compressed against the roughened lower surface of the second flat extending portion 170a, locking the two together and locking the length of the cross-link.

Once the length of the cross-link is been set, the set screws 120 may be tightened down, thereby locking the element 100a and 160a to the rods themselves.

Referring now to FIGS. 5b, 7, 8, and 9b, the second alternative embodiment of this invention is now described. This embodiment is designed for coupling the rod apparatuses of the dual rod implant construct together by joining to the pedicle screws themselves. More specifically, with respect to the first element 100b shown in FIG. 5b, the element comprises a first end 102b which is flat and includes a through hole 103. This through hole 103 is provided such that the top of a pedicle screw may be inserted therein, and such that the top locking nut of the pedicle screw may be threaded down onto the head of the pedicle screw, thereby securing the element 100b to the rod assembly.

Figure 5B:
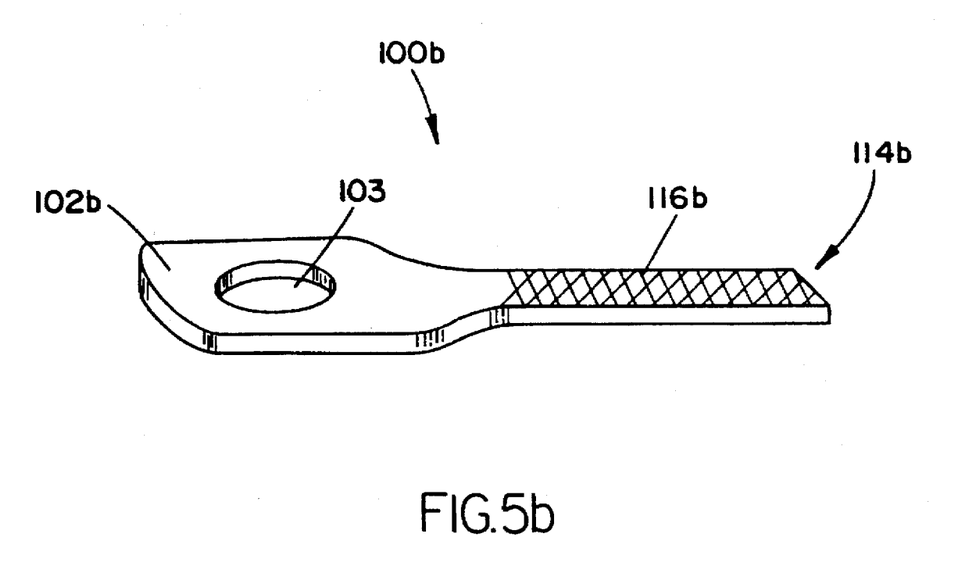

The other end 114b of this first element 100b is identical in every respect to the second end 114a of the first element 100a as shown in FIG. 5a. Similarly, the post 130a and nut 150 elements utilized in conjunction with this second embodiment are identical to the ones used in conjunction with the first embodiment.

Figure 9B:
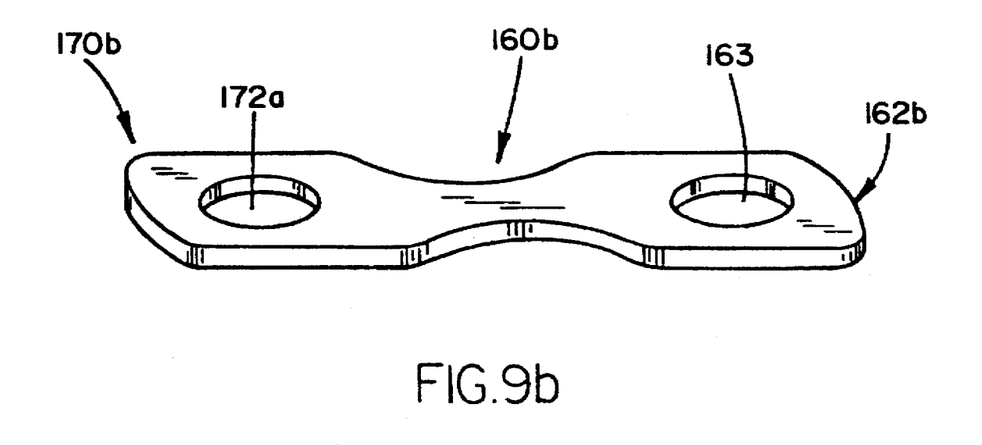

Referring now to FIG. 9b, the second element 160b of this second embodiment is provided. It comprises a first rod assembly securing end 162b, which includes a through hole 163 which is similar in form and function to the through hole 103 of the first element 100b of this second embodiment. More specifically, this hole 163 is provided to receive the head of a pedicle screw, and to provide secure coupling thereto upon the subsequent engagement of a top locking nut onto the head of the pedicle screw. The second end 170b of this second element 160b comprises the same structure and features as the second end of the second element 160a as shown and described with respect to FIG. 9a.

Figure 10B:
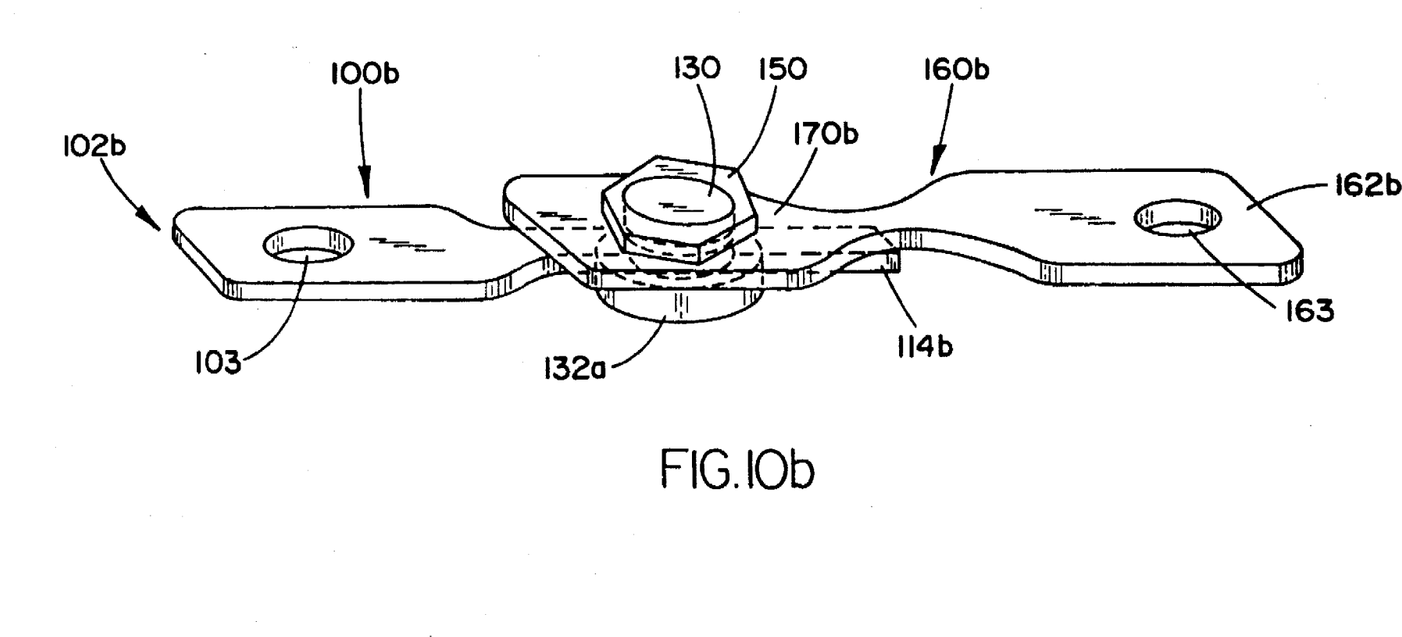
FIG. 10b is a side perspective view of a fully assembled embodiment of the present invention comprising all of the elements illustrated in FIGS. 5b, 7–8, and 9b.

Referring now also to FIG. 10b, in which the fully assembled cross-link device, the elements of which are set forth in FIGS. 5b, 7, 8, and 9b, is shown in a side perspective view, the implantation of this second embodiment is described. As above, the narrow and flat extending portion 114b of the first element 100b is inserted into the passageway 136 of the post 130a, such that the roughened top surface 116b of the extending portion 114b is oriented in the direction of the upper section 138a of the post 130a. Then the upper section 138a of the post 130a is inserted through the hole 172b in the rod coupling flat extending portion 170b of the second element 160b. The post 130a is inserted upwardly so that the top locking nut 150, and more specifically the threads 156 thereof, may engage the threads 140a of the upper portion 138a. Initial tightening of the nut 150 downward on the post 130a causes the bottom surface 154 of the nut to seat against the top surface of the flat extending portion 170b. At this point the flat extending portion 114b of the first element 100b remains slidable relative to both the post 130a and the second element 160b. In this way, the rod securing portions 102b and 162b may be selectively spread or drawn together and angulated within the plane defined by the two elements.

In this untightened configuration, the rod coupling ends 102b and 162b of the device are positioned over the heads of the pedicle screws such that the heads of the screws extend upwardly through the holes 103 and 163, respectively. By tightening the locking nuts of the pedicle screws down, the elements 100b and 160b are locked in position.

Continued tightening of the nut 150 causes the post 130a to be drawn upwards through the hole 172b, thereby causing the intermediate section, and the passageway 136 thereof to be similarly drawn upwards. In doing so, the roughened top surface 116b of the narrowed flat extending portion 114b is compressed against the roughened lower surface of the second flat extending portion 170b, locking the two together and locking the length of the cross-link.

Figure 11:
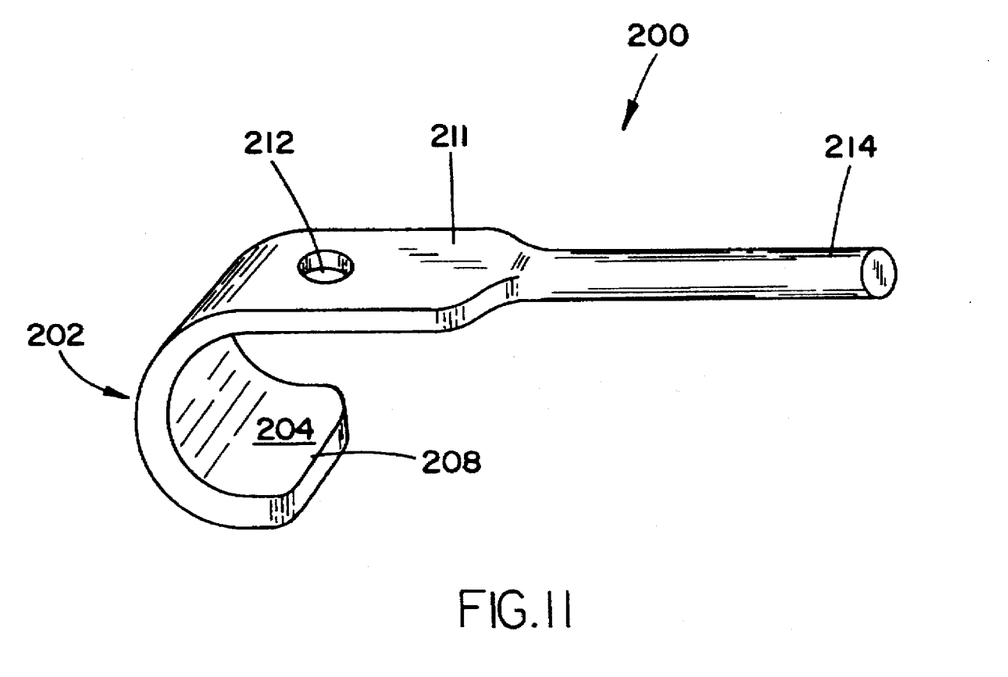
FIG. 11 is a side perspective view of an alternative first element.

Referring now to FIG. 11, an alternate first element 200 which corresponds to a third embodiment of the present invention is shown. This embodiment further provides the cross-link with the ability to accommodate pairs of rods which are locally not co-planar (they are contoured such that the rod and/or coupling sites would not securely receive parallel coupling hooks or eyeloops). This embodiment is described with respect to a variation which is similar to the first embodiment inasmuch as it couples to the rods, not to the pedicle screws, and is locked to the rods with set screws in a similar manner.

More specifically with respect to the first element 200 shown in FIG. 11, the first (rod coupling) end 202 of which has been curved to the shape of a hook. As with the first element 100a of the first embodiment, the hook has a semi-circular curvature defined by an inner surface 204. The lower portion 208 of the semi-circular hook extends tangentially for a small distance, parallel to the remainder of the element. The curve is semi-circular so that it can cup and hook to the lateral outside surface of a first rod of a dual rod apparatus. The top portion 211 of the first end 202 comprises a through hole 212 which is threaded to receive a set screw 120 to lock the element 200 to the rod of the implant assembly.

The other end 214 of the rod coupling element comprises the distinctive feature of this embodiment, as compared with the first elements 100a, 100b of the first and second embodiments. It comprises a cylindrical shaft. This shaft may include a surface roughening, for example a diamond knurling, for locking within the post element 130b.

Figure 12:
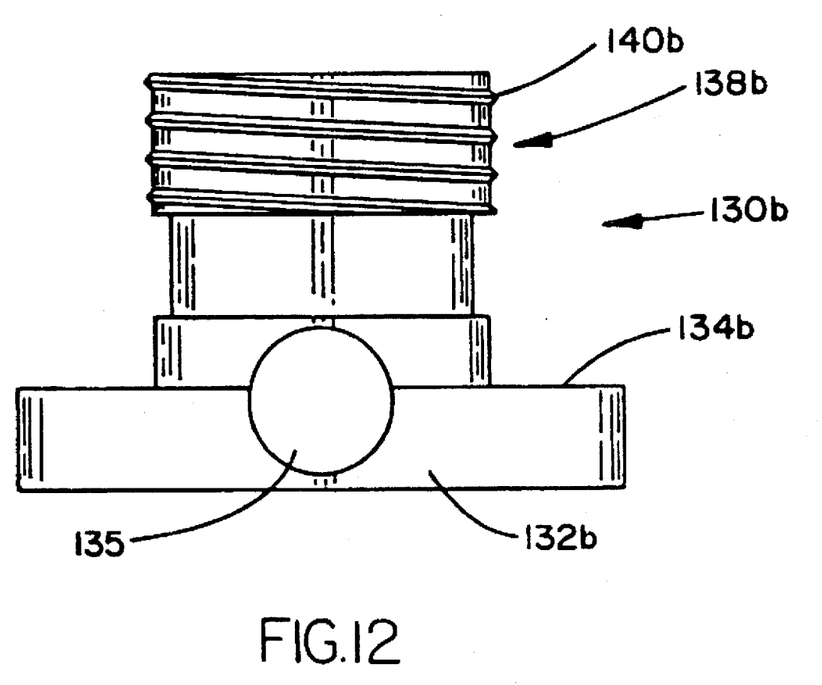
FIG. 12 is a side view of an alternative post member having a cylindrical passageway.

Referring now to FIG. 12, a side view of the post 130b which corresponds to this third embodiment is provided. As previously described, the post 130b has a generally cylindrical shape. The base 132b of the post is wider than the upper portions, forming an annular flange 134b. The upper portion of the base 132b, and the lower portion of the intermediate section of the post 130b includes a cylindrical passageway 135 which extends transverse to the axis of the post. This passageway 135 is ideally suited for slidably receiving therethrough the shaft 214 of the first rod coupling element 200. The diameter of the passageway 135 is desirably slightly larger than the thickness of the shaft 214, such that the shaft 214 may slide and rotate therein (such that the length of the device, and the relative angulation of the rod coupling ends may be easily selected).

As set forth above with respect to the first two embodiments, the upper portion 138b of the post 130b extends upward from the passageway 136 and the intermediate portion, and comprise a threading 140b which is ideally suited for receiving thereon a top locking nut 150 (as shown in FIG. 8).

Figure 13:
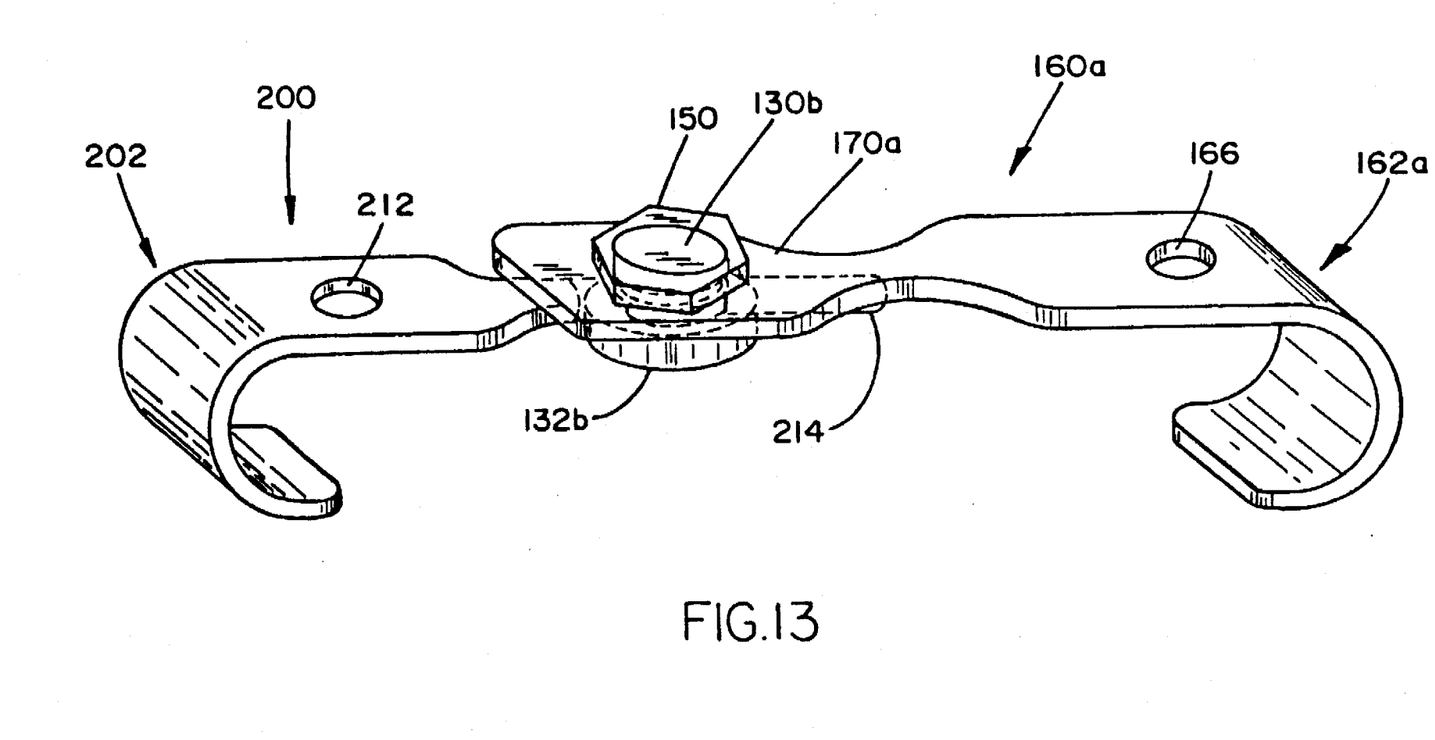
FIG. 13 is a side perspective view of a fully assembled alternative embodiment of the present invention which includes the elements illustrated in FIGS. 5a, 6, 8, 9a, 11, and 12.

Referring now to FIG. 13, in which an assembled device corresponding to this third embodiment is shown in a side prespective view. The second element of this device is identical to the second element 160a of the first embodiment (it being understood that if this third embodiment is to be coupled to the pedicle screws, then the second element would be identical to the second element 160b of the second embodiment). First the proper site on the rods for the fixation of the cross-link device is identified by the surgeon. The site should provide enough space along the rods for engagement of rod securing ends 202 and 162a. Once this site is found, and the space separating the rods is cleared of all obstacles (for example, the spinous process) the shaft 214 of the first element 200 is inserted into the cylindrical passageway 135 of the post 130b, such that the shaft is axially rotatable and translatable within the passageway 135.

Once the shaft 214 has been inserted, the upper section 138b of the post 130b is inserted through the hole 172a in the rod coupling flat extending portion 170a of the second element 160a. The post 130b is inserted upwardly so that the top locking nut 150, and more specifically the threads 156 thereof, may engage the threads 140b of the upper portion 138b. Initial tightening of the nut 150 downward on the post 130b causes the bottom surface 154 of the nut to seat against the top surface of the flat extending portion 170a. At this point the shaft 214 of the first element 200 remains slidable and rotatable relative to both the post 130b and the second element 160a. The rod securing portions 202 and 162a may be selectively spread or drawn together by an amount determined solely by the length of the shaft 214. In addition, the elements 200,160a may be rotated within the plane defined thereby. Further, the elements 200,160a, and the rod securing ends 202,162a thereof, may be axially rotatable relative to one another via rotation of the shaft 214 within the passage 135.

Continued tightening of the nut 150, however, causes the post 130b to be drawn upwards through the hole 172a, thereby causing the intermediate section, and the passageway 135 thereof to be similarly drawn upwards. In doing so, the roughened surface of the narrowed shaft 214 is compressed against the roughened lower surface of the second flat extending portion 170a, locking the two together and locking the length of the cross-link. In addition, the compressive force applied to the shaft 214 by the lower surface of the second end 170a of the second element 160a causes the roughened surface of the shaft 214 to bind to the inner surface of the passageway 135, thereby further crush locking the device into a rigid configuration.

Once the length of the cross-link is been set, the set screws 120 may be tightened down, thereby locking the element 200 and 160a to the rods themselves.

While there have been described and illustrated cross-link devices for coupling dual rods of orthopaedic apparatus together and providing enhanced stability thereto, it will be apparent to those skilled in the art that variations and modifications are possible without deviating from the broad spirit and principle of the present invention which shall be limited solely by the scope of the claims appended hereto.

We claim:

1. A variable length cross-link device for use with orthopaedic rod apparatuses having a plurality of rods, comprising:

a first element having first and second ends, said first end including means for coupling to a first rod, said second end comprising a narrow extending portion;

a second element having first and second ends, said first end including means for coupling to a second rod, said second end comprising a wide extending portion, said wide extending portion including a through hole;

a post including an upper portion having a threading thereon, said upper portion being mounted through the through hole in the second element; and a lower portion having a passageway therethrough for receiving said narrow extending portion of said first element, such that said second end of said second element seats around said post at a position above said passageway; and a nut, threadably engageable with the upper portion of the post, whereby prior to tightening of the nut on the post, the first element is slideable relative to the post and the second element, and the post element has rotational freedom within the through hole such that the first and second elements may be angulated relative to one another, and whereby tightening of the nut on the post causes the first and second elements to be compressibly engaged, thereby crush locking the elements together.

2. The cross-link device as set forth in claim 1, wherein the means for coupling the first and second elements to the first and second rods, respectively, comprise set screws and hook shaped first ends having threaded holes therethrough for receiving said set screws.

3. The cross-link device as set forth in claim 1, wherein the means for coupling the first and second elements to the first and second rods, respectively, comprise eyeloops formed in the first ends thereof, which eyeloops are positionable over respective heads of pedicle screws, whereby each element is coupled to the corresponding pedicle screw by a nut.

4. The cross-link device as set forth in claim 1, wherein the narrow extending portion of the first element comprises a cylindrical shaft, and wherein the passageway through the post is correspondingly cylindrical, such that the first element may also be axially rotatable relative to the second element.

5. The cross-link device as set forth in claim 1, further comprising a surface roughening disposed on the narrow extending portion of the first element and the wide extending portion of the second element.

6. The cross-link device as set forth in claim 5, further comprising a surface roughening disposed on an interior surface of said passageway of said post.

7. The cross-link device as set forth in claim 5, wherein said roughened surface comprises a diamond knurl.

8. The cross-link device as set forth in claim 6, wherein said roughened surface comprises a diamond knurl.

9. A cross-linked dual rod orthopaedic implant apparatus comprising:
 a pair of rods adapted to be coupled to posterior surfaces of sequential vertebrae via pedicle screws;
 at least one variable length cross-link device for coupling said pair of rods, including
  a first element having first and second ends, said first end including means for coupling to a first rod, said second end comprising a narrow extending portion;
  a second element having first and second ends, said first end including means for coupling to a second rod, said second end comprising a wide extending portion, said wide extending portion including a through hole;
  a post including an upper portion having a threading thereon, said upper portion being mounted through the through hole in the second element; and a lower portion having a passageway therethrough for receiving said narrow extending portion of said first element, such that said second end of said second element seats around said post at a position above said passageway; and
  a nut, threadably engageable with the upper portion of the post,
 whereby prior to tightening of the nut on the post, the first element is slideable relative to the post and the second element, and the post element has rotational freedom within the through hole such that the first and second elements may be angulated relative to one another, and whereby tightening of the nut on the post causes the first and second elements to be compressibly engaged, thereby crush locking the elements together.

10. The apparatus as set forth in claim 9, wherein the means for coupling the first and second elements to the first and second rods, respectively, comprise set screws and hook shaped first ends having threaded holes therethrough for receiving said set screws.

11. The apparatus as set forth in claim 9, wherein the means for coupling the first and second elements to the first and second rods, respectively, comprise eyeloops formed in the first ends thereof, which eyeloops are positionable over respective heads of pedicle screws, whereby each element is coupled to the corresponding pedicle screw by a nut.

12. The apparatus as set forth in claim 9, wherein the narrow extending portion of the first element comprises a cylindrical shaft, and wherein the passageway through the post is correspondingly cylindrical, such that the first element may also be axially rotatable relative to the second element.

13. The apparatus as set forth in claim 9, further comprising a surface roughening disposed on the narrow extending portion of the first element and the wide extending portion of the second element.

14. The apparatus as set forth in claim 13, further comprising a surface roughening disposed on an interior surface of said passageway of said post.

15. The apparatus as set forth in claim 14, wherein said roughened surface comprises a diamond knurl.

16. The apparatus as set forth in claim 13, wherein said roughened surface comprises a diamond knurl.

* * * * *